United States Patent [19]

Bower et al.

[11] Patent Number: 5,257,540
[45] Date of Patent: Nov. 2, 1993

[54] PORTABLE APPARATUS FOR MEASURING FORCE AND POWER SUPPLIED TO A PEDAL-DRIVEN CYCLE

[76] Inventors: Grant L. Bower, 6201 Ravenna Ave., NE., Seattle, Wash. 98115; Charles A. Kingsford-Smith, 405 8th St., Mukilteo, Wash. 98275; Terry E. McIlraith, 407 Castello Rd., Lafayette, Calif. 94549

[21] Appl. No.: 771,192

[22] Filed: Oct. 4, 1991

[51] Int. Cl.$^5$ .............................................. A61B 5/22
[52] U.S. Cl. .............................. 73/379.07; 73/862.326; 482/900
[58] Field of Search ............ 73/379, 862.324, 862.325, 73/862.326, 862.328, 862.337, 379.06, 379.07; 482/57, 63, 900, 901, 909

[56] References Cited

U.S. PATENT DOCUMENTS

| | | | |
|---|---|---|---|
| 3,939,932 | 2/1976 | Rosen | 73/379 X |
| 4,519,603 | 5/1985 | DeCloux | 482/63 X |
| 4,520,681 | 6/1985 | Moore et al. | 73/862.324 X |
| 4,811,612 | 3/1989 | Mercat | 73/862.324 |
| 4,875,379 | 10/1989 | Rohs et al. | 73/862.326 |
| 5,027,303 | 6/1991 | Witte | 73/379 X |
| 5,031,455 | 7/1991 | Cline | 73/862.328 X |
| 5,067,354 | 11/1991 | Kawai | 73/862.328 |

Primary Examiner—Donald O. Woodiel
Assistant Examiner—Elizabeth L. Dougherty
Attorney, Agent, or Firm—Charles A. Kingsford-Smith

[57] ABSTRACT

An instrumentation system for measuring the instantaneous pedal force and power exerted by the rider of a cycle is described. Being small and lightweight, it is intended to be mounted on the cycle and to operate while the cycle is ridden. The pedal crank assembly is modified to provide an elastic support for the chainring assembly, allowing a small relative rotation between pedals and chainrings when force is applied to the pedals. This rotation is a function of the magnitude of the force and is detected by angle detectors, consisting of angle indicators rotating with the pedal crank assembly and stationary sensors mounted on the cycle frame. These angle detectors measure the relative rotation at 25 or more positions distributed around a revolution of the pedal crank assembly. Electrical signals from the sensors are coupled to a microprocessor. The processor compares the signals, computes the applied pedal force and power at each measurement position, and displays and/or stores the results. A procedure is given for individually calibrating each measurement, thereby greatly reducing repetitive errors.

7 Claims, 6 Drawing Sheets

PORTABLE APPARATUS FOR MEASURING FORCE AND POWER SUPPLIED TO A PEDAL-DRIVEN CYCLE

BACKGROUND OF THE INVENTION a) Field of the invention

This invention relates to pedal-driven cycles, such as bicycles, and specifically to a means for instrumenting a cycle in order to measure the force and power imparted to the pedals by the rider as he rides the cycle along a pathway.

b) Description of related art

Early bicycle instruments were primarily 1) speedometers for speed measurements and 2) stationary dynamometers to measure power and torque. Speedometers were mechanical and very similar 20 to the common automotive variety. They have been almost completely replaced by lightweight electronic units. Dynamometers also were, and are, similar to the automotive variety. The bicycle is mounted in a stationary support, and the drivewheel is held in contact with an instrumented roller which absorbs power.

What has been lacking until recent years is a useful method of measuring the power generated by a cycle rider as he pedals his cycle along a path. (When "power" measurement is used in this discussion, it is understood that torque and pedal force are also available, since all three quantities are readily deduced from the same measured data.) The scarcity of portable power measuring instruments is mainly due to not having a suitable elastic element in the drive train.

In recent years, a few attempts have been made to measure this "on the road" power. Clearly, such measuring devices must be lightweight and must process the data acquired, display it to the rider, and/or store it. Two such devices are described in the prior art section of U.S. Pat. No. 4,811,612 (Mercat, issued Mar. 14, 1989). The first device determines the tension of the drive chain by measuring the deflection of a spring-loaded roller in contact with the chain. The second device uses a special driving hub in which there are two elements coupled by an elastic member. When torque is applied to the hub, there is a relative angular movement between these elements, which is then measured and converted to a torque reading. This latter method is an example of the most common technique of torque measurement: determining the relative rotation of the end portions of an elastic element which forms part of the power transmission train.

Mercat teaches an ingenious use of this torque measurement technique. In this patent, the drivewheel itself contains the elastic element, which is the array of spokes connecting the driving hub with the wheel rim. As torque is applied to the hub, the spokes are slightly stretched, allowing relative rotation between hub and rim. Photoelectric sensors are used to generate signals related to hub and rim rotation, and these signals are manipulated in a microprocessor to compute the applied torque and power. The apparatus can, in principle, be made light and small enough to be carried on the bicycle.

Nevertheless, Mercat has several disadvantages which limit its utility. One is that the drivewheel must be substantially modified. The spokes must be removed from the usual alternately forward- and rearward-sloping attachment to the hub and fastened radially to it. In addition, the mathematical rule of correspondence, relating the relative hub-to-rim rotation with the applied torque, has both a linear and a cubic term. This non-linearity makes it a practical necessity to use a microprocessor to compute the torque and power.

Another disadvantage is that the measurement is made at the rear drivewheel, not at the pedal assembly. Between these locations, the power values are different because of friction losses in the drivetrain. The torque values are different because of these losses and also because the rider frequently changes gear ratios. It is evident that a rider would like to maintain a level of effort consistent with his level of physical fitness. Yet without a knowledge of the drivetrain friction loss and gear ratio, the microprocessor can compute neither the rider's power output nor his pedal force from drivewheel measurements.

An additional limitation occurs in all designs, including Mercat, which do not directly measure the rider's power input to the pedals. They are unable to determine the individual effort of each of the rider's legs. Yet this information would be a valuable aid in his training regimen.

SUMMARY

According to the invention, a system is provided for measuring the force imparted to the pedals of the pedal crank assembly of a cycle type vehicle. This system relies on the introduction of an elastic support structure between a) the axle, on the ends of which the pedal crank arms are rigidly mounted, and b) the chainring assembly. (The term "chainring assembly" refers to one or more annular discs of different sizes forming a rigid assembly, with each disc having circumferential teeth .) The elastic support structure is preferably implemented in the form of a solid disc in which a number of radial slots have been cut. The slots increase the elasticity in the rotational direction. Thus, when axle torque, caused by application of force to the pedals, is applied to the disc for transmittal to the chainring assembly, the increased elasticity of the disc results in a relative rotation of its inner and outer radial surfaces. Since the axle is firmly secured to the inner surface and the chainring assembly to the outer, a relative rotation also takes place between these elements.

This relative rotation between axle and chainring assembly provides the ability to measure the axle torque, and therefore the pedal force which produced it. Angle detectors, described below, detect the angular positions of the axle and the chainring assembly. A microprocessor coupled to the detectors determines the differential rotation of the axle and the chainring assembly, and computes the torque and power by means well known in the prior art.

The angle detectors consist of two angle indicators rotating with the pedal crank assembly and two stationary sensors attached to the cycle frame. In a preferred realization of the invention, one angle indicator is a chainring itself, and a sensor detects the passage of its teeth, thus providing information about the instantaneous position of the chainring assembly. A second sensor determines the position of the axle by sensing the teeth (or equivalent) of a second angle indicator attached to the axle. As the pedal assembly revolves, the electrical signals from these sensors approximate rectangular pulse trains. It is well known that the time difference between these signals contains the information needed to compute torque. Dividing the torque by the pedal moment arm yields pedal force, and multiplying this force by the signal frequency results in a quantity proportional to power.

A feature of the invention is generating an index signal once per revolution of the pedal assembly, enabling the microprocessor to identify the absolute angular position of the pedals. The index signal can be used to distinguish the force applied to the left pedal from that applied to the right.

More importantly, the index signal serves as the basis for an error-canceling calibration technique. The torque information is derived from the time shift between pairs of teeth on the two angle indicators. For angle indicators with n teeth, there are thus measurements of torque possible in each revolution of the pedals. These measurements are subject to repetitive errors of several kinds. Examples of such error sources are random manufacturing variations in the width of each tooth, and angle indicators not being quite concentric with the axle.

These repetitive errors are overcome in the invention by a novel calibration procedure. Using the index signal to define an initial position, the teeth on the angle indicators are enumerated in sequence from 1 to n. (Identically numbered teeth on each angle indicator comprise a "pair".) During calibration, the pedals are rotated without load (that is, with zero force) and the microprocessor measures the time shifts for each of the n pairs of teeth. It then computes and stores an individual calibration constant for each pair. During normal pedaling, these stored constants are then used to correct each pair's contribution to the determination of pedal force.

OBJECTS OF THE INVENTION

According to the detailed description contained herein, it is an object of the invention to provide an apparatus for determining the pedal force and power a rider imparts to the powertrain of a cycle-type vehicle, such as a bicycle, in order to propel the vehicle.

It is a further object of the invention that the apparatus be small in size, lightweight, non-intrusive to the rider's movements and control of the cycle, and non-energy-absorbing. These features will allow the determination of the pedal force and power while the cycle is ridden on a pathway.

It is a still further object of the invention to measure the pedal force and power at the input of the power train, rather than at some other location, such as the drive wheel. By observing the power at the input, energy losses in the power train and transmission gear ratios do not affect the measurement of the rider's effort.

Most prior techniques in the field of measuring torque and power average the measurement over one or more revolutions of the rotating structure. At times, averaging is a natural consequence of a particular measuring technique. Often, averaging is deliberately introduced to reduce the effect of undesirable disturbances, both mechanical and electrical. In contrast to this, an additional object of the invention is to determine instantaneous, not average, pedal force and power at small angular increments of the position of the pedal crank, thus revealing the large natural variation of these quantities over a revolution of the pedal crank assembly.

These and other objects are brought out in the detailed description.

DETAILED DESCRIPTION

Figure 1:
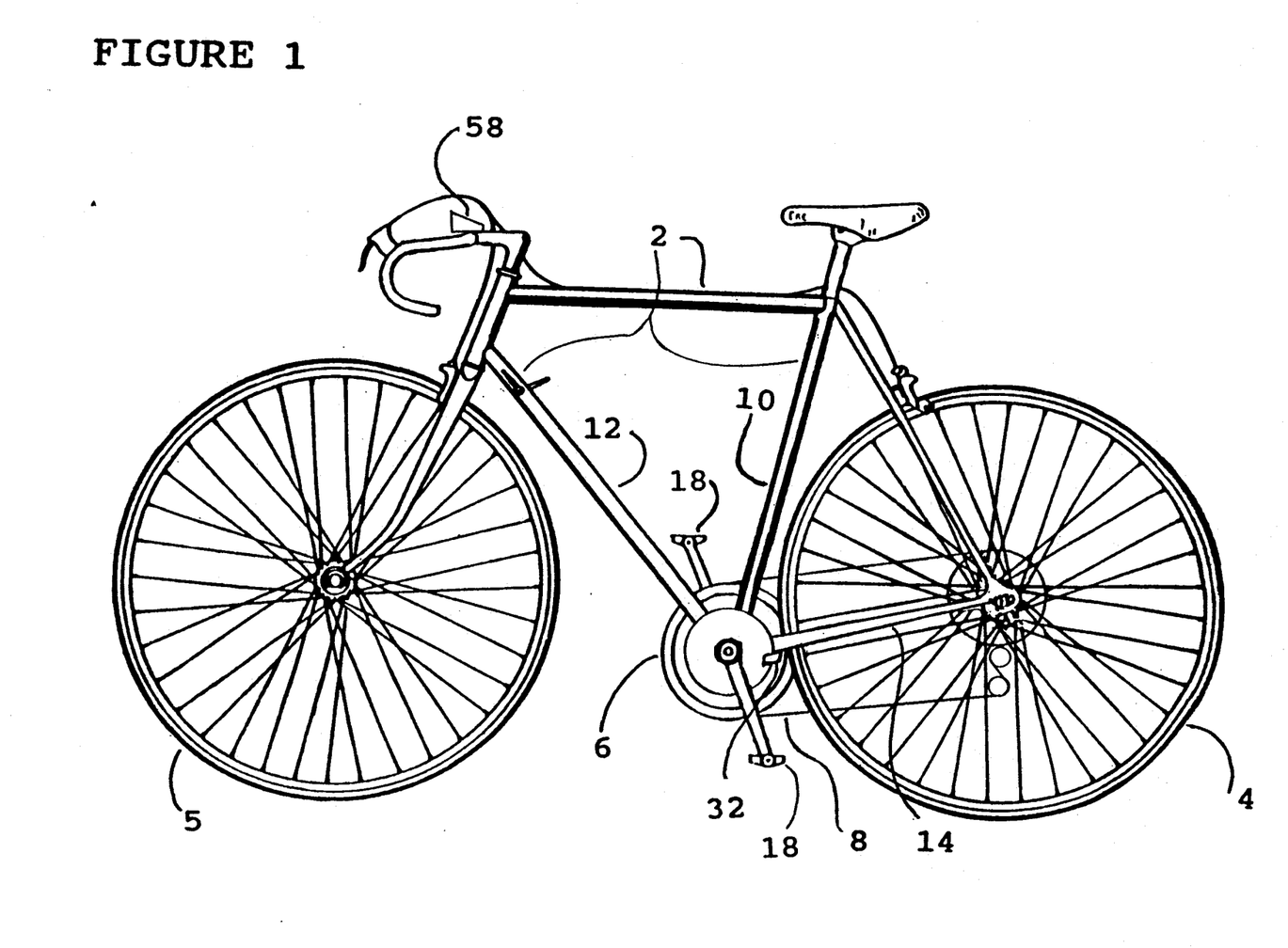
FIG. 1 overall view of bicycle

FIG. 1 shows the principle elements of a conventional bicycle as they relate to the present invention. A rider sits astride the frame 2 of the bicycle, positioning his feet on the pedals 18 of the pedal crank assembly 6. This assembly, rotatably mounted in the frame 2, revolves because of the forces the rider applies to the pedals. A continuous chain 8 links the pedal crank assembly 6 and a drive wheel 4, also rotatably mounted in the frame 2. Because of this linkage, the power delivered by the rider to the pedals of the pedal crank assembly 6 (less some unavoidable mechanical losses) is transformed into rotation of the drivewheel 4, thus propelling the bicycle and rider along a pathway.

Figure 2:
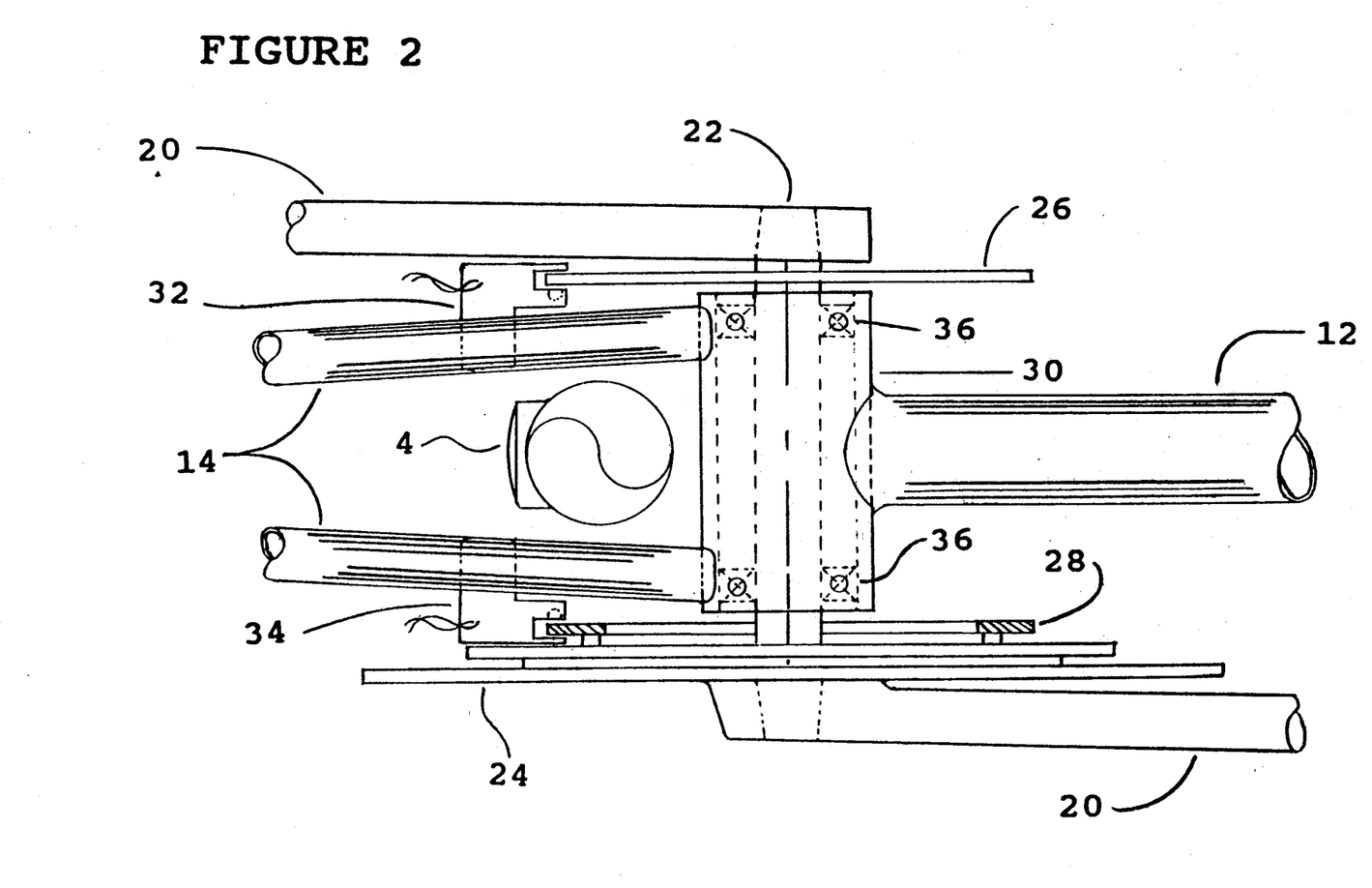
FIG. 2 pedal crank assembly mounted in frame, top view
Figure 3:
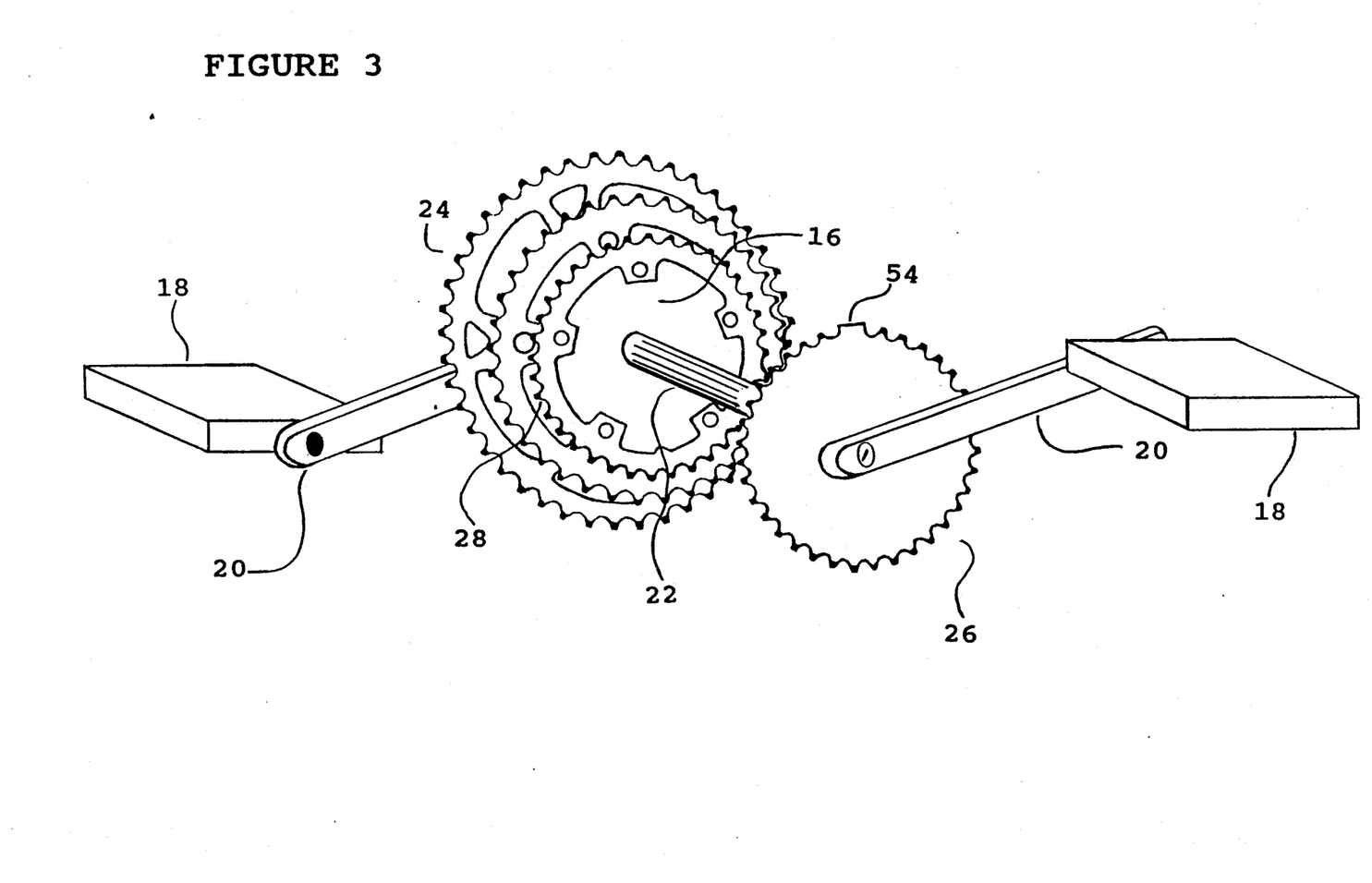
FIG. 3 pedal crank assembly removed from frame

Referring to FIGS. 2 and 3, it will be seen that the pedal crank assembly 6 comprises four principle elements: a) a pair of pedals 18, each rotatably mounted on one end of its respective pedal crank arm 20; b) an axle 22 rotatably supported on bearings 36 in the frame 2 in a transverse horizontal position; c) a chainring assembly 24, comprising at least one chainring, but usually several chainrings of various diameters rigidly fastened together as shown; d) a supporting structure 16 which fastens the chainring assembly 24 to the axle 22.

The pedal crank arms 20 are attached, at right angles, to opposite ends of the axle 22. The arms project in opposite directions from the axle 22; that is, in directions 180 degrees apart in the sense of angular rotation of the axle 22. As the rider applies force to the pedals 18, that component of force normal to both the crank arms 20 and the axle 22 produces a rotational force (that is, torque) in the axle 22. Since the axle 22 is firmly attached to the chainring supporting structure 16, and the latter, in turn, is firmly attached to the chainring assembly 24, the result is that the entire pedal crank assembly 6 rotates around the axis of the axle 22. Chainrings are annular discs with a toothed circumference, the pitch of which matches the pitch of the chain 8, which wraps around approximately half the circumference, as can be seen in FIG. 1. Consequently, applying force to the pedals 18 causes a a tensile force to be applied to the chain 8, and the chain, on the rearward portion of its travel, engages another chainring mounted to the drivewheel 4, causing a rotational force to be applied to the drivewheel. Thus, the pedals 18 form the first element, and the drivewheel 4 the last element, of a powertrain conveying power (sometimes called tractive effort) from the rider's legs to the surface of the roadway.

Figure 4:
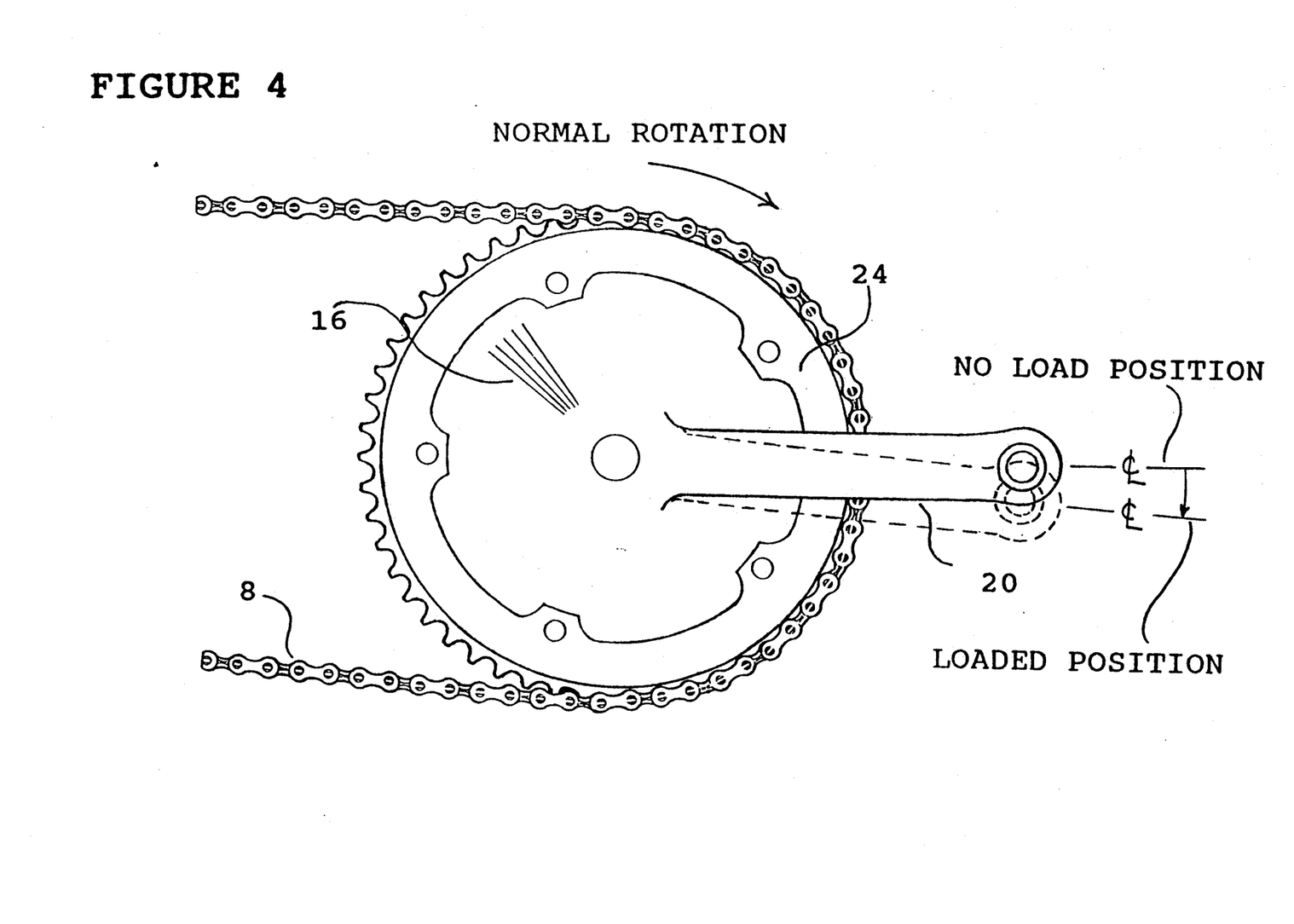
FIG. 4 view of pedal crank assembly showing effect of pedal force on chainring supporting structure FIG. 5. Idealized angle detector FIG. 6 electrical signals generated by sensors of the angle detectors

In this invention, a modification is made to the chainring support structure 16 to allow for a relative rotation between the chainring assembly 24 and the axle 22, as force is applied to the pedals 18. This relative rotation under applied pedal force is obtained by increasing the elasticity of the chainring support structure 16 in the circumferential direction, while largely retaining the original rigidity of the structure in the radial and axial directions. (All directions refer to the orientation of the axle 22.) A preferred means of accomplishing this is to build the support structure 16 in the form of an annular disc of sufficient thickness to provide axial and radial rigidity, yet with a large number of narrow, radially-oriented slots, as shown in FIG. 4. It is important to maintain both axial and radial rigidity in the support structure 16. This rigidity is needed to prevent any significant displacement of the chainring position relative to other elements of the pedal crank assembly 6.

Another means of obtaining the same properties just described is to use a support structure 16 made of a solid anisotropic material, oriented such that the elasticity in the circumferential direction is much greater than in the other two directions.

As the rider presses on the pedals, producing a torque in the axle 22, the inner radial surface of the elastic supporting structure 16, which is firmly attached to the axle 22, rotates relative to the outer radial surface, which is firmly attached to the chainring assembly 24. The amount of rotation is a function of the geometry of the support structure 16, its modulus of elasticity, and the torque in the axle 22. The direction of this relative rotation is such that the axle 22 advances in the direction of its rotation, relative to the chainring assembly 24, when force is applied to the pedals.

A maximum relative rotation of about 5 degrees allows for good measurement sensitivity, while avoiding a "spongy" pedal characteristic for the rider. Likewise, such a small deflection of the support structure means the relative rotation is linearly related to torque, thus simplifying later computations.

Figure 5:
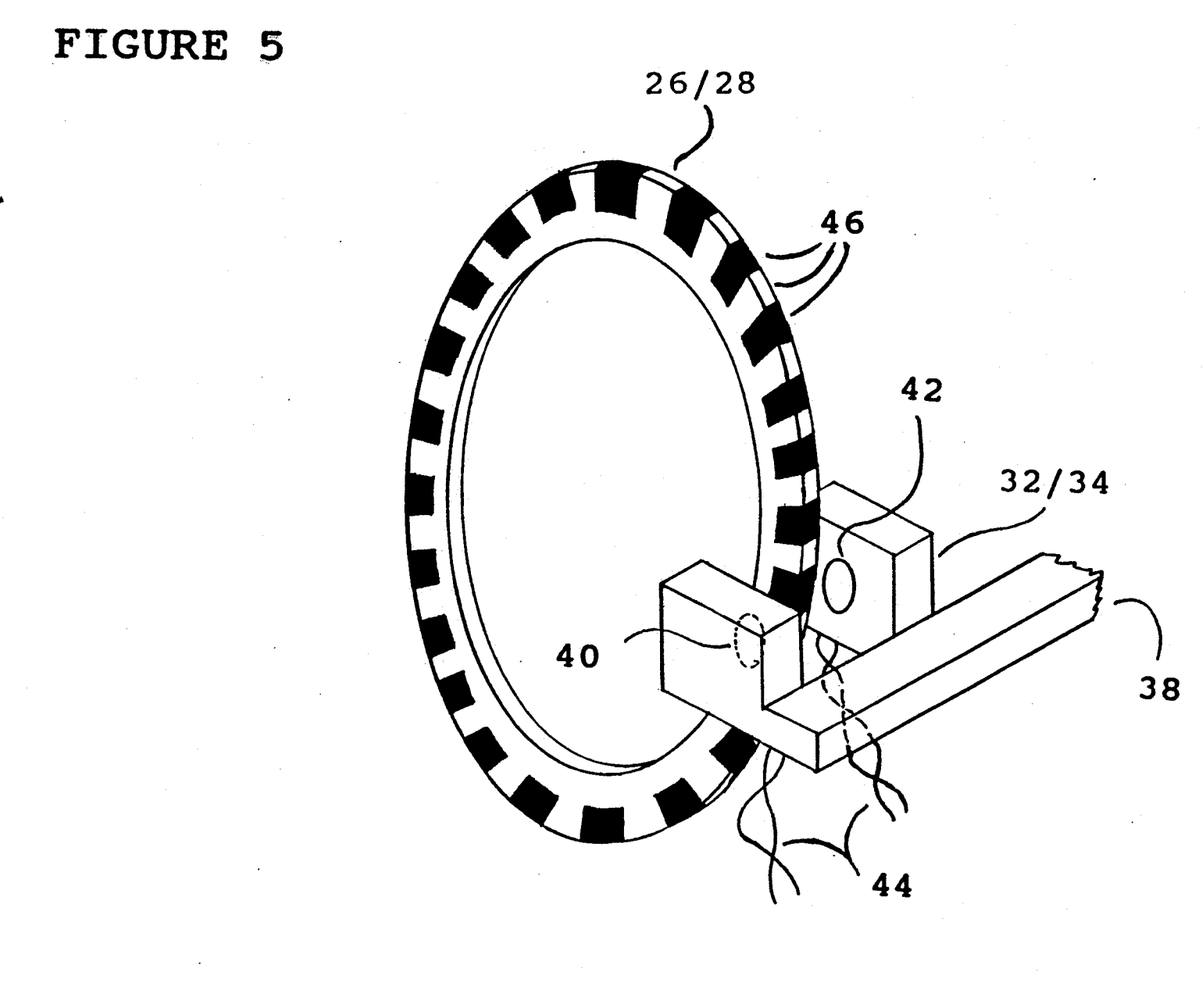

To detect the angular rotation of both axle 22 and chainring assembly 24, two sensors are used, a first sensor 32 and a second sensor 34 (FIGS. 2 and 5). These sensors are fixed to the frame and detect, respectively, the motion of two angle indicators, a first angle indicator 26 and a second angle indicator 28. Except for details of their mounting to the frame, these sensors are similar and each consists of a light emitter 40 (infrared radiation emitting diode) mounted oppositely facing a light detector 42 (photo diode or transistor), the two being held rigidly in a mounting bracket 38. Wires 44 attach to the sensor to bring electrical power to the light emitter 40 and to convey signals from the light detector 42 to the microprocessor 58.

As FIG. 5 indicates, the first angle indicator 26 is a disklike structure with a series of contiguous areas 46 of alternatively strong (preferably transparent) and weak (preferably opaque) light transmission, spaced uniformly around the disk at a fixed radius. The first angle indicator 26 must rotate with the axle 22. The number of areas of opaque light transmission in the first angle indicator 26 should equal the number of teeth of the second angle indicator 28. A separately mounted chainring can be used effectively as the first angle indicator 26.

The second angle indicator 28 is also a disclike structure and is, preferably, a chainring in the chainring assembly 24. The second sensor 34 is mounted astride the chainring so that the light passing from its emitter 40 to its detector 42 is interrupted by the teeth of the chainring as the latter rotates.

Figure 6:
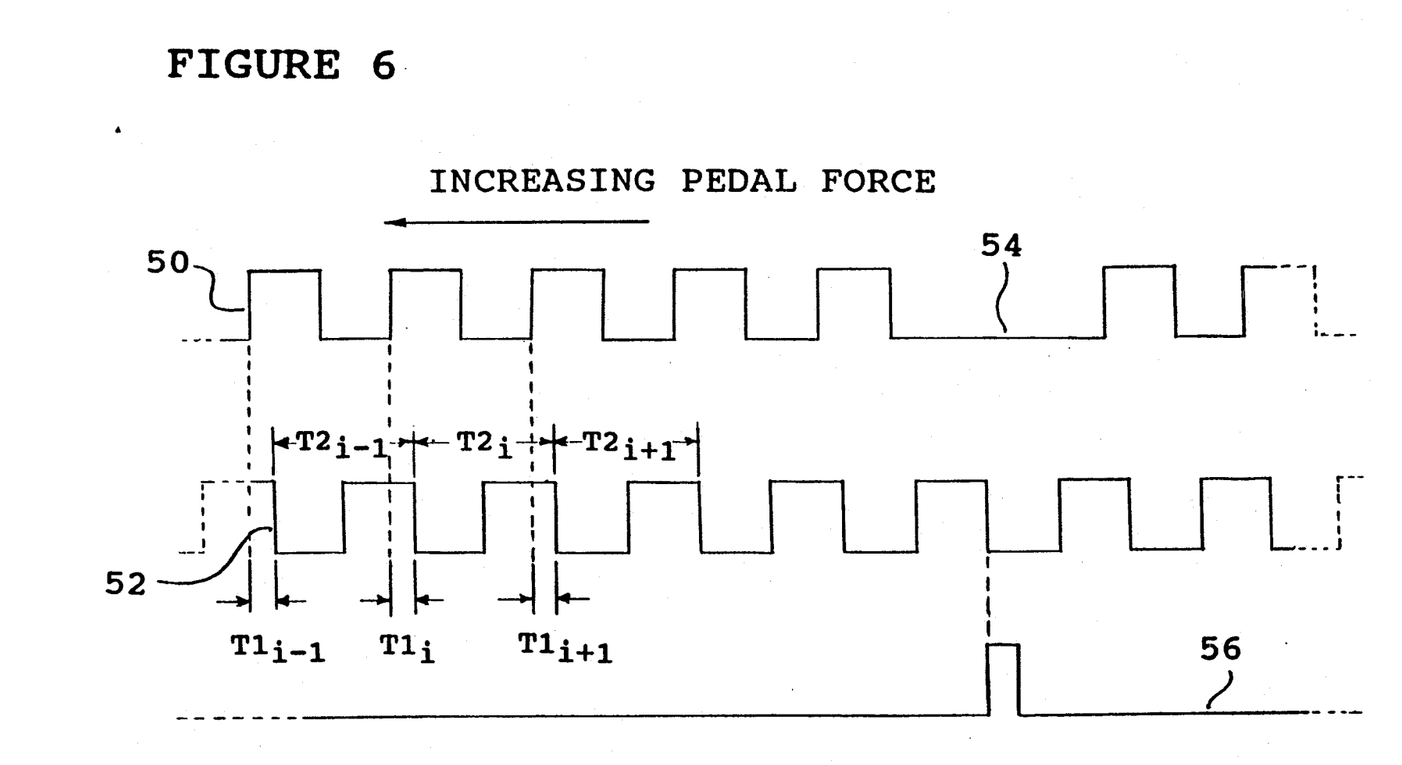

Rotation of the first and second angle indicators 26 and 28 causes repetitive interruptions of the light beams of the respective sensors 32 and 34. Consequently, the respective light detectors 40 of the sensors 32 and 34 generate electrical output signals approximating squarewaves, as shown in FIG. 6. The polarity of these squarewaves 50 and 52 is such that positive excursions represent light transmission from the emitters 40 to the detectors 42.

Squarewave signals 50 and 52 contain information relative to the instantaneous force applied by the rider to the pedals and to the rotational speed of the pedal crank assembly 6. To extract this and other information, the signals 50 and 52 are coupled to the microprocessor 58 which performs algorithmic operations on them. The nature of the signals and of the algorithmic operations will now be described in sufficient detail to be clear to those skilled in the signal processing arts.

In FIG. 6, signals 50 and 52 are shown as being nearly in phase opposition; that is, a positive edge of signal 50 occurs just before a negative edge of signal 52. This condition is obtained by adjusting the physical position of both angle indicators 26 & 28 and their respective sensors 32 and 34 such that one of the light detectors 42 is illuminated while the other is dark. The waveforms in FIG. 6 represent the signals generated when the pedal crank assembly is rotating with negligible force applied to the pedals 18; for instance, when the chain 8 is disconnected. This is referred to as the "zero-force" condition. However, when a tractive effort is required to accelerate or to overcome normal losses associated with bicycle motion, the rider applies force to the pedals 18. Because of the elasticity of the chainring support structure 16, the angular position of axle 22 advances relative to that of chainring assembly 24 and, consequently, signal 50 advances in time with respect to signal 52. This relative advance is indicated by a left shift of signal 50.

In this embodiment of the invention, the microprocessor 58 computes four basic types of information:
1) Zero-force calibration data
2) Pedal force
3) Power input to pedals
4) Pedal assembly rotational speed Details of these measurements and computations are now described:

1) Zero-force calibration. The measurement of force in this invention is based on measuring the relative rotation of two components in a powertrain coupled by an elastic element. Accordingly, it is necessary to measure (and store) the initial relative rotational positions of these components—i.e., their at-rest or zero-force positions—in order to have an accurate basis for subsequent force measurements.

In FIG. 6, intervals of time are expressed in seconds. The interval $T1_i$ is a measure of the relative position of the angle indicators 26 and 28. This is the ith such measure, out of n similar measures, where n is the number of opaque areas 46 of an angle indicator, typically in the range of 25 to 50. However, $T1_i$ varies both with the angular displacement of the angle indicators and (inversely) with the rotational speed of the pedal crank assembly 6. But, by dividing $T1_i$ by the interval $T2_i$, a quantity $C_i = T1_i/T2_i$ is formed, which is a measure of angular displacement and is invariant with rotational speed of the pedal crank assembly 6. The n values of $C_i$ which are so computed form the ordered set of zero-force calibration constants. It is evident that each of the n constants is dependent on the actual transition times of its corresponding areas 46, as these areas pass through the sensors. Therefore, any repetitive irregularities—those due to manufacturing variations, for instance—are reflected in the stored constants.

In order to identify each $C_i$ with the pairs of physical areas 46 (one on each angle indicator 26 and 28) corresponding to it, it is necessary to provide an index or synchronizing signal once per revolution of the pedal crank assembly. This signal allows the microprocessor 58 to order, store, and retrieve the values of C as required. A preferred means of doing this is shown in waveform 50. One normally transparent area of the angle indicator 26 has been made opaque, causing one positive excursion of signal 50 to be missing. The required index signal 56 is determined by the occurrence of a negative transition of waveform 52 when waveform 50 is low. This procedure requires the sacrifice of one of the n possible measurements around a full revolution of the pedal crank assembly. However, this loss is negligible if the index signal 56 occurs when the pedal crank arms 20 are vertical, a position where the pedal force is usually very small. If the full complement of n measurements is required, a way to achieve this is to use a third sensor to detect the passage of a pedal crank arm 20 past a fixed location on the frame 2.

2) Pedal force. Using the index signal to identify the start of the succession of areas 46 through the sensors, the microprocessor 58 measures each interval $T1_i$ and $T2_i$, retrieves each calibration constant $C_i$, and computes the quantity $$\text{Force}_i = (T1_i/T2_i - C_i)K$$

where K is a force constant dependent on the geometry of the pedal crank assembly 6 and the elasticity of the support structure 16. K is readily determined, using a known weight and a dial gauge, using this procedure:
 a) attach the known weight W to a pedal 18
 b) measure the resulting angular displacement D between axle 22 and chainring assembly 24. Express D as a fraction of the angular tooth-to-tooth spacing of the chainring used as the second angle indicator 28.
 c) compute $K = W/D$ It is clear that it is possible to measure n independent, individually calibrated values of force during a revolution of the pedal crank assembly 6. The microprocessor 58 may display these values numerically or graphically as instantaneous force, may average them over an interval, may store them for later analysis, or may perform other useful operations on the data.

3) Power input to pedals. Having computed pedal force, and knowing the time T2, it is a simple matter to compute the instantaneous power. The formula for the power during the ith interval is $$\text{Power}_i = (\text{Force}_i)(1/T2_i)(M)$$

where M is a constant. If power is in watts, pedal force in pounds, and R is the pedaling radius (length of the crank arm 20) in feet, then $$M = (2\pi/n)(R)(1.36)$$

4) Pedal assembly rotational speed. The value, in instantaneous RPM, is $(n)(1/T2)(60)$. Although the preferred embodiment has been described in detail, it should be understood that various changes, substitutions and alterations can be made therein without departing from the spirit and scope of the invention as defined by the appended claims.

We claim:

1. An apparatus for measuring forces applied to the pedals of a pedal-driven cycle by a rider thereof, comprising:
 a) a pedal crank assembly comprising:
  a1) an axle rotatably mounted in the frame of the cycle, having first and second ends;
  a2) a first pedal crank arm having an end attached to the first end of the axle and another end on which is attached a first pedal for exerting a first torsional force on the axle;
  a3) a second pedal crank arm having an end attached to the second end of the axle and another end on which is attached a second pedal for exerting a second torsional force on the axle;
  a4) a chainring assembly, comprising at least one chainring located coaxially with the axle;
  a5) a supporting structure, composed at least partially of elastic material, for supporting the chainring assembly on the axle to rotate therewith, having one surface fixedly attached to the axle and another surface fixedly attached to the chainring assembly, such that coupling the torsional forces from the axle to the supporting structure distorts the elastic material in a known manner, thereby varying the angular position of the chainring assembly relative to the angular position of the axle;
 b) first angle detecting means for sensing the angular position of the axle and generating a first electrical signal related thereto, comprising:
  b1) a first angle indicator, coupled with the axle and rotating therewith;
  b2) a first sensor, mounted on the frame proximate the first angle indicator;
 c) second angle detecting means for sensing the angular position of the chainring assembly and generating a second electrical signal related thereto, comprising:
  c1) a second angle indicator, coupled with the chainring assembly and rotating therewith;
  b2) a second sensor, mounted on the frame proximate the second angle indicator;
 d) signal processing means, coupled to the first and second electrical signals, for deriving data related to the relative angular positions of the axle and the chainring assembly, and for computing, from these data, the forces applied to the pedals.

2. The apparatus of claim 1 in which:
 a) the first and second angle indicators each comprise a disc, located coaxially with and perpendicular to the axle, each disk containing, at the same radial distance from the axle, a series of contiguous areas of different light-transmitting characteristics with a sharply defined boundary between adjacent areas;
 b) the first and second sensors each comprise a light emitting source located facing a light sensitive detector positioned so that the light energy from the source reaches the detector only after having traversed the contiguous areas of the corresponding angle indicating disc, whereby the rotation of the disc causes the contiguous areas to pass sequentially between the source and the detector, causing magnitude transitions of the light energy reaching the detector and corresponding transitions in the electrical signal generated by the detector.

3. The apparatus of claim 2 in which the second angle indicating disc is a chainring selected from the chainring assembly.

4. The apparatus of claim 1 in which:
a) the first and second angle indicators each comprise a disc, located coaxially with and perpendicular to the axle, each disk containing, at the same radial distance from the axle, a series of contiguous areas of different magnetic properties with a sharply defined boundary between adjacent areas;
b) the first and second sensors each comprise a magnetic detector positioned sufficiently proximate the contiguous areas of the corresponding disc that rotation of the disc causes transitions in the electrical signals from the detector.

5. The apparatus of claim 1 in which:
a) the first and second angle indicators each comprise a disc, located coaxially with and perpendicular to the axle, each disk containing, at the same radial distance from the axle, a series of contiguous areas of different electrically conductive properties with a sharply defined boundary between adjacent areas;
b) the first and second sensors each comprise a capacitative detector positioned sufficiently proximate the contiguous areas of the corresponding disc that rotation of the disc causes transitions in the electrical signals from the detector.

6. The apparatus of claim 1 in which the signal processing means additionally derives data related to the absolute angular velocity of the pedal crank assembly and computes the power applied to the pedals.

7. A calibration method for reducing systematic errors in an apparatus for measuring the forces applied to the pedals of a cycle, the apparatus including
1) a pedal crank assembly axle coupled to a chainring assembly by an elastic supporting structure;
2) a first angle indicating means, coupled to the axle, having dissimilar areas separated by sharp boundaries;
3) a second angle indicating means, coupled to the chainring assembly, having dissimilar areas separated by sharp boundaries;
4) sensors, responsive to the dissimilar areas, proximate each angle indicating means, for generating electrical sensor signals with sharp transitions:
5) means for generating an electrical index signal;
6) a signal processor, responsive to the electrical signals, for computing the applied forces;
the method comprising the steps of:
a) determining and storing a numerical error-correcting constant for each dissimilar area on said first and second angle indicating means by employing the steps of:
a1) establishing a "zero force" reference by rotating said pedal crank assembly while supplying negligible propulsive force;
a2) sequentially enumerating the electrical signal transitions, beginning at the time the index signal is generated;
a3) deriving, for each enumerated signal transition, "zero force" data related to the relative angular position between the axle and the chainring assembly;
a4) storing the "zero force" data in a reference table indexed to the enumerated signal transitions;
b) accessing the data stored in the reference table to reduce systematic measurement errors incurred while a rider is supplying propulsive force to the cycle, by identifying each signal transition in the same manner as in (a2) and using the corresponding stored datum as an individual "zero-force" reference quantity when computing the applied forces.

* * * * *